(12) United States Patent
Bennett et al.

(10) Patent No.: US 6,214,986 B1
(45) Date of Patent: Apr. 10, 2001

(54) ANTISENSE MODULATION OF BCL-X EXPRESSION

(75) Inventors: C. Frank Bennett, Carlsbad, CA (US); Nicholas M. Dean, Olivenhain, CA (US); Brett P. Monia, LaCosta, CA (US); Brian J. Nickoloff, Burr Ridge, IL (US); QingQing Zhang, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/323,743

(22) Filed: Jun. 2, 1999

Related U.S. Application Data

(63) Continuation-in-part of application No. 09/277,020, filed on Mar. 26, 1999, and a continuation-in-part of application No. 09/167,921, filed on Oct. 7, 1998.

(51) Int. Cl.$^7$ .......................... C07H 21/04; C07H 21/02; C12Q 1/68; A01N 43/04; A61K 31/70
(52) U.S. Cl. ................ 536/24.5; 536/23.1; 536/24.3; 536/24.33; 435/6; 435/91.1; 435/325; 435/375; 514/44
(58) Field of Search ................... 536/23.1, 24.3, 536/24.5, 24, 24.33; 435/6, 325, 375, 91.1; 514/44

(56) References Cited

U.S. PATENT DOCUMENTS

| | | | |
|---|---|---|---|
| 5,034,506 | * 7/1991 | Summerton et al. | 528/391 |
| 5,652,355 | * 11/1997 | Metelev et al. | 536/24.5 |
| 5,834,309 | * 11/1998 | Thompson et al. | 435/325 |
| 5,856,462 | * 1/1999 | Agrawal | 536/24.5 |

OTHER PUBLICATIONS

Andrea D. Branch, A good antisense molecule is hard to find, TIBS, 47–48, Feb. 1998.*
Trisha Gura, Antisense Has Growing Pains, Science, pp. 575–577, Oct. 1995.*
Stanley T. Crooke, Basic Principles of Anitsense Therapeutics, Springer–Verlag, NY, p. 3, Jul. 1998.*
The above cited references are not provided, copies of these references were previously sent to Applicant accompanying parent application: 09/167,921.*
Decaudin et al. Bcl–2 and Bcl–Xl antagonize the mitochondrial dysfunction preceeding nuclear apoptosisi . . . , Cancer Res. vol. 57, pp. 62–67, Jan. 1997.*
Srinivasan et al. Bcl–xL functions downstream of Caspase–8 . . . , JBC. vol. 273. No. 8. pp. 4523–4529, Feb. 1998.*
Tu et al. BCl–X Expression in myeloma: Possible Indicator of Chemoresistance. cancer res. vol. 58. pp. 256–262, Jan. 1998.*

* cited by examiner

Primary Examiner—Robert A. Schwartzman
Assistant Examiner—Janet Epps
(74) Attorney, Agent, or Firm—Law Offices of Jane Massey Licata

(57) ABSTRACT

Compositions and methods are provided for modulating the expression of bcl-x. Antisense compounds, particularly antisense oligonucleotides, targeted to nucleic acids encoding bcl-x are preferred. Methods of using these compounds for modulation of bcl-x expression and for treatment of diseases associated with expression of bcl-x are also provided. Methods of sensitizing cells to apoptotic stimuli are also provided.

50 Claims, No Drawings

ANTISENSE MODULATION OF BCL-X EXPRESSION

The present application is a continuation-in-part of U.S. patent application 09/277,020, filed Mar. 26, 1999 and of U.S. patent application 09/167,921, filed Oct. 7, 1998.

FIELD OF THE INVENTION

The present invention provides compositions and methods for modulating the expression of bcl-x. In particular, this invention relates to antisense compounds, particularly oligonucleotides, specifically hybridizable with nucleic acids encoding human bcl-x. Such oligonucleotides have been shown to modulate the expression of bcl-x.

BACKGROUND OF THE INVENTION

Programmed cell death, or apoptosis, is an essential feature of growth and development, as the control of cell number is a balance between cell proliferation and cell death. Apoptosis is an active rather than a passive process, resulting in cell suicide as a result of any of a number of external or internal signals. Apoptotic cell death is characterized by nuclear condensation, endonucleolytic degradation of DNA at nucleosomal intervals ("laddering") and plasma membrane blebbing. Programmed cell death plays an essential role in, for example, immune system development and nervous system development. In the former, T cells displaying autoreactive antigen receptors are removed by apoptosis. In the latter, a significant reshaping of neural structures occurs, partly through apoptosis.

An increasing number of genes and gene products have been implicated in apoptosis. One of these is bcl-2, which is an intracellular membrane protein shown to block or delay apoptosis. Overexpression of bcl-2 has been shown to be related to hyperplasia, autoimmunity and resistance to apoptosis, including that induced by chemotherapy (Fang et al., *J. Immunol.* 1994, 153, 4388–4398). A family of bcl-2-related genes has been described. All bcl-2 family members share two highly conserved domains, BH1 and BH2. These family members include, but are not limited to, A-1, mcl-1, bax and bcl-x. Bcl-x was isolated using a bcl-2 cDNA probe at low stringency due to its sequence homology with bcl-2. Bcl-x was found to function as a bcl-2-independent regulator of apoptosis (Boise et al., *Cell,* 1993, 74, 597–608). Two isoforms of bcl-x were reported in humans. Bcl-xl (long) contains the highly conserved BH1 and BH2 domains. When transfected into an IL-3 dependent cell line, bcl-xl inhibited apoptosis during growth factor withdrawal in a manner similar to bcl-2. In contrast, the bcl-x short isoform, bcl-xs, which is produced by alternative splicing and lacks a 63-amino acid region of exon 1 containing the BH1 and BH2 domains, antagonizes the anti-apoptotic effect of either bcl-2 or bcl-xl. As numbered in Boise et al., *Cell,* 1993 74:, 597–608, the bcl-x transcript can be categorized into regions described by those of skill in the art as follows: nucleotides 1–134, 5' untranslated region (5'-UTR); nucleotides 135–137, translation initiation codon (AUG); nucleotides 135–836, coding region, of which 135–509 are the shorter exon 1 of the bcl-xs transcript and 135–698 are the longer exon 1 of the bcl-xl transcript; nucleotides 699–836, exon 2; nucleotides 834–836, stop codon; and nucleotides 837–926, 3' untranslated region (3'-UTR). Between exons 1 and 2 (between nucleotide 698 and 699) an intron is spliced out of the pre-mRNA when the mature bcl-xl (long) mRNA transcript is produced. An alternative splice from position 509 to position 699 produces the bcl-xs (short) mRNA transcript which is 189 nucleotides shorter than the long transcript, encoding a protein product (bcl-xs) which is 63 amino acids shorter than bcl-xl. Thus nucleotide position 698 is sometimes referred to in the art as the "5' splice site" and position 509 as the "cryptic 5' splice site," with nucleotide 699 sometimes referred to as the "3' splice site."

Diseases and conditions in which apoptosis has been implicated fall into two categories, those in which there is increased cell survival (i.e., apoptosis is reduced) and those in which there is excess cell death (i.e., apoptosis is increased). Diseases in which there is an excessive accumulation of cells due to increased cell survival include cancer, autoimmune disorders and viral infections. Until recently, it was thought that cytotoxic drugs killed target cells directly by interfering with some life-maintaining function. However, of late, it has been shown that exposure to several cytotoxic drugs with disparate mechanisms of action induces apoptosis in both malignant and normal cells. Manipulation of levels of trophic factors (e.g., by anti-estrogen compounds or those which reduce levels of various growth hormones) has been one clinical approach to promote apoptosis, since deprivation of trophic factors can induce apoptosis. Apoptosis is also essential for the removal of potentially autoreactive lymphocytes during development and the removal of excess cells after the completion of an immune or inflammatory response. Recent work has clearly demonstrated that improper apoptosis may underlie the pathogenesis of autoimmune diseases by allowing abnormal autoreactive lymphocytes to survive. For these and other conditions in which insufficient apoptosis is believed to be involved, promotion of apoptosis is desired. This can be achieved, for example, by promoting cellular apoptosis or by increasing the sensitivity of cell to endogenous or exogenous apoptotic stimuli, for example, cell signaling molecules such as $TNF\alpha$ or other cytokines, cytotoxic drugs or radiation. Promotion of or sensitization to apoptosis is believed to have clinical relevance in, for example, sensitizing cancer cells to chemotherapeutic drugs or radiation. It is also believed to be relevant in blocking angiogenesis which is necessary for tumor growth. This is because tumor cells release angiogenic factors to recruit angiogenic endothelial cells to the tumor site. It would be desirable to sensitize these angiogenic endothelial cells to apoptotic stimuli (chemotherapeutic drugs, radiation, or endogenous $TNF\alpha$) to block angiogenesis and thus block tumor growth. Aberrant angiogenesis is also implicated in numerous other conditions, for example macular degeneration, diabetic retinopathy and retinopathy of prematurity, all of which can cause loss of vision. Aberrant angiogenesis is also implicated in other, non-ocular conditions. Thus "aberrant" angiogenesis can refer to excessive or insufficient angiogenesis, or undesired angiogenesis (as, for example, in the case of angiogenesis which supports tumor growth. Blocking aberrant angiogenesis by sensitizing angiogenic endothelial cells to apoptotic stimuli is therefore desired.

In the second category, AIDS and neurodegenerative disorders like Alzheimer's or Parkinson's disease represent disorders for which an excess of cell death due to promotion of apoptosis (or unwanted apoptosis) has been implicated. Amyotrophic lateral sclerosis, retinitis pigmentosa, and epilepsy are other neurologic disorders in which apoptosis has been implicated. Apoptosis has been reported to occur in conditions characterized by ischemia, e.g. myocardial infarction and stroke. Apoptosis has also been implicated in a number of liver disorders including obstructive jaundice and hepatic damage due to toxins and drugs. Apoptosis has also been identified as a key phenomenon in some diseases of the kidney, i.e. polycystic kidney, as well as in disorders of the pancreas including diabetes (Thatte, et al., *Drugs,* 1997, 54, 511–532). For these and other diseases and conditions in which unwanted apoptosis is believed to be involved, inhibitors of apoptosis are desired.

Antisense oligonucleotides have been used to elucidate the role of several members of the bcl-2 family. Extensive studies using antisense oligonucleotides targeted to bcl-2 have been performed, and an antisense compound (G3139, Genta Incorporated) targeted to human bcl-2 has entered clinical trials for lymphoma and prostate cancer.

Amarante-Mendes et al., *Oncogene,* 1998, 16, 1383–1390, disclose antisense oligonucleotides targeted to bcr and bcl-x. The latter downregulated the expression of bcl-xl and increased the susceptibility of HL-60 Bcr-Abl cells to staurosporine.

U.S. Pat. No. 5,583,034 (Green et al.) discloses antisense oligonucleotides which hybridize to the nucleic acid sequence of an anti-apoptotic gene, preferably to the translation start site of bcr-abl.

Wang et al. used a phosphorothioate oligonucleotide targeted to the bcl-x translation start site to block CD40L-mediated apoptotic rescue in murine WEHI-231 lymphoma cells (*J. Immunol.,* 1995, 155, 3722–3725).

Fujio et al. have used an antisense oligodeoxynucleotide targeted to murine and rat bcl-x mRNA to reduce bcl-xl protein expression (*J. Clin. Invest.,* 1997, 99, 2898–2905). The compound tested was the same as that of Wang et al. Oligonucleotide treatment inhibited the cytoprotective effect of leukemia inhibitory factor in mouse or rat cardiac myocytes Pollman et al. used antisense oligodeoxynucleotides with phosphorothioate backbones to downregulate bcl-xl expression in blood vessel intimal cells (*Nature Med.,* 1998, 4, 222–227). This resulted in induction of apoptosis and regression of vascular lesions. Antisense sequences were targeted to the translation initiation codon of mouse/human bcl-x (conserved sequence) and were used in rabbits. Gibbons et al., U.S. Pat. No. 5,776,905, disclose methods for targeted deletion of intimal lesion cells in the vasculature of a mammal with vascular disease, preferably with antisense molecules specific for anti-apoptotic genes, more preferably bcl-x and most preferably bcl-xl.

Thompson et al., U.S. Pat. No. 5,646,008 and WO 95/00642 describe an isolated and purified polynucleotide that encodes a polypeptide other than bcl-2 that promotes or inhibits programmed vertebrate cell death. Preferably the polypeptide is bcl-xl, bcl-xs or bcl-$x_1$. Polypeptides, polynucleotides identical or complementary to a portion of the isolated and purified polynucleotide, expression vectors, host cells, antibodies and therapeutic and diagnostic methods of use are also provided.

Yang et al., WO 98/05777 disclose bcl-xγ (gamma), a novel isoform of the bcl-x family which includes an ankyrin domain. Polypeptide and nucleic acid sequences for this isoform are disclosed, as well as, inter alia, methods for modulating bcl-xγ activity, including antisense methods.

SUMMARY OF THE INVENTION

The present invention is directed to antisense compounds, particularly oligonucleotides, which are targeted to a nucleic acid encoding bcl-x, and which modulate the expression of bcl-x. Pharmaceutical and other compositions comprising the antisense compounds of the invention are also provided. Further provided are methods of modulating the expression of bcl-x in cells or tissues comprising contacting said cells or tissues with one or more of the antisense compounds or compositions of the invention. Further provided are methods of treating an animal, particularly a human, suspected of having or being prone to a disease or condition associated with expression of bcl-x by administering a therapeutically or prophylactically effective amount of one or more of the antisense compounds or compositions of the invention.

DETAILED DESCRIPTION OF THE INVENTION

The present invention comprehends antisense compounds capable of modulating expression of human bcl-x and of its isoforms, bcl-xl and bcl-xs. Bcl-xl inhibits apoptosis and therefore inhibitors of bcl-xl, particularly specific inhibitors of bcl-xl such as the antisense compounds of the present invention, are desired as promoters of apoptosis. In contrast, the bcl-x short isoform, bcl-xs, antagonizes the anti-apoptotic effect and therefore promotes apoptosis. Inhibitors of bcl-xs are desired as inhibitors of apoptosis. Antisense compounds which specifically inhibit the expression of a particular isoform, either bcl-xl or bcl-xs, of bcl-x, or which alter the expression ratio of these two isoforms, are particularly useful for both research and therapeutic, including prophylactic, uses.

The present invention employs oligomeric antisense compounds, particularly oligonucleotides, for use in modulating the function of nucleic acid molecules encoding bcl-x, ultimately modulating the amount of bcl-x produced. This is accomplished by providing antisense compounds which specifically hybridize with one or more nucleic acids encoding bcl-x. As used herein, the terms "target nucleic acid" and "nucleic acid encoding bcl-x" encompass DNA encoding bcl-x, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of bcl-x. In the context of the present invention, "modulation" means either an increase (stimulation) or a decrease (inhibition) in the expression of a gene product. In the context of the present invention, inhibition is a preferred form of modulation of gene expression and mRNA is a preferred target. Further, since many genes (including bcl-x) have multiple transcripts, "modulation" also includes an alteration in the ratio between gene products, such as alteration of mRNA splice products.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding bcl-x. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed MRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding bcl-x, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N ($CH_3$)—O—$CH_2$— [known as a methylene (methylimino) or MMI backbone], —$CH_2$—O—N ($CH_3$) —$CH_2$—, —$CH_2$—N ($CH_3$)—N ($CH_3$)—$CH_2$— and —O—N ($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nNH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes an alkoxyalkoxy group, 2'-methoxyethoxy (2'-O-$CH_2CH_2OCH_3$, also known as 2'-O-(2-methoxyethyl) or 2'-MOE) (Martin et al., *Helv. Chim. Acta,* 1995, 78, 486–504). A further preferred modification includes 2'-dimethylaminooxyethoxy, i.e., a $O(CH_2)_2ON(CH_3)_2$ group, also known as 2'-DMAOE.

Other preferred modifications include 2'-methoxy (2'-O-$CH_3$), 2'-aminopropoxy (2'-$OCH_2CH_2CH_2NH_2$) and $2^1$-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the reparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering,* pages 858–859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Crooke, S. T., and Lebleu, B. eds., *Antisense Research and Applications,* CRC Press, Boca Raton, 1993, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications,* CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 25 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 or in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred addition salts are acid salts such as the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embolic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of bcl-x is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding bcl-x, enabling sandwich and other assays to easily be constructed to exploit this fact. Hybridization of the antisense oligonucleotides of the invention with a nucleic acid encoding bcl-x can be detected by means known in the art. Such means may include conjugation of an enzyme to the oligonucleotide, radiolabelling of the oligonucleotide or any other suitable detection means. Kits using such detection means for detecting the level of bcl-x in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems,* 1991, 8, 91–192; Muranishi, *Critical Reviews in Therapeutic Drug Carrier Systems,* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, 8:2, 91–192; Muranishi, *Critical Reviews in Therapeutic Drug Carrier Systems,* 1990, 7:1, 1–33; El-Hariri et al., *J. Pharm. Pharmacol.,* 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, 8:2, 92–192; Muranishi, *Critical Reviews in Therapeutic Drug Carrier Systems,* 1990, 7:1, 1–33; Buur et al., *J. Control Rel.,* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, 8:2, 92–191); and perfluorochemical emulsions, such as FC-43 (Takahashi et al., *J. Pharm. Pharmacol.,* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems,* 1991, 8:2, 92–191); and non-steroidal anti-inflammatory agents such as diclofenac sodium, indomethacin and phenylbutazone (Yamashita et al., *J. Pharm. Pharmacol.,* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. No. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.,* 1995, 6, 698–708).

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy,* 15th Ed., Berkow et al., eds., 1987, Rahway, N.J., pp. 1206–1228. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pp. 2499–2506 and 46–49, respectively. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods (Sanghvi, et. al., *Nucleic Acids Research*, 1993, 21, 3197–3203] using commercially available phosphoramidites (Glen Research, Sterling, Va. or ChemGenes, Needham, Mass.).

2'-Fluoro amidites

2'-Fluorodeoxyadenosine amidites

2'-fluoro oligonucleotides were synthesized as described previously by Kawasaki, et. al., *J. Med. Chem.*, 1993, 36, 831–841 and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid that was crushed to a light tan powder (57 g, 85% crude yield). The NMR spectrum was consistent with the structure, contaminated with phenol as its sodium salt (ca. 5%). The material was used as is for further reactions or purified further by column chromatography using a gradient of methanol in ethyl acetate (10–25%) to give a white solid, mp 222–4° C.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH4OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-ethylcytidine (74 g, 0.10 M) was dissolved in $CH_2Cl_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaRCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as per the phosphodiester oligonucleotides except the standard oxidation bottle was replaced by 0.2 M solution of 3H-1,2- benzodithiole-3-one 1,1-dioxide in acetonitrile for the stepwise thiation of the phosphite linkages. The thiation wait step was increased to 68 seconds and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl hosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phoshorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides are synthesized via solid phase P(III) phosphoramidite chemistry on an automated synthesizer capable of assembling 96 sequences simultaneously in a standard 96 well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites are purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides are cleaved from support and deprotected with concentrated NH$_4$OH at elevated temperature (55–60° C.) for 12–16 hours and the released product then dried in vacuo. The dried product is then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well is assessed by dilution of samples and UV absorption spectroscopy. The full-length integrity of the individual products is evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition is confirmed by mass analysis of the compounds utilizing electrospray-mass spectroscopy. All assay test plates are diluted from the master plate using single and multi-channel robotic pipettors. Plates are judged to be acceptable if at least 85% of the compounds on the plate are at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR, RNAse protection assay (RPA) or Northern blot analysis. The following four human cell types are provided for illustrative purposes, but other cell types can be routinely used.

T-24 cells:

The transitional cell bladder carcinoma cell line T-24 is obtained from the American Type Culture Collection (ATCC) (Manassas, Va.). T-24 cells are routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reached 90% confluence. Cells are seeded into 96-well plates (Falcon-Primaria #3872) at a density of 7000 cells/well for use in RT-CR analysis.

For Northern blotting or other analysis, cells may be seeded onto 100 mm or other standard tissue culture plates and treated similarly, using appropriate volumes of medium and oligonucleotide.

A549 cells:

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reached 90% confluence.

NHDF cells:

Human neonatal dermal fibroblast (NHDF) are obtained from the Clonetics Corporation (Walkersville, Md.). NHDFs are routinely maintained in Fibroblast Growth Medium (Clonetics Corporation, Walkersville, Md.) supplemented as recommended by the supplier. Cells are maintained for up to 10 passages as recommended by the supplier.

HEK cells:

Human embryonic keratinocytes (HEK) are obtained from the Clonetics Corporation (Walkersville, Md.). HEKs are routinely maintained in Keratinocyte Growth Medium (Clonetics Corporation, Walkersville Md.) formulated as recommended by the supplier. Cells are routinely maintained for up to 10 passages as recommended by the supplier.

Treatment with antisense compounds:

When cells reached 80% confluency, they are treated with oligonucleotide. For cells grown in 96-well plates, wells are washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired oligonucleotide at a final concentration of 150 nM. After 4 hours of treatment, the medium is replaced with fresh medium. Cells are harvested 16 hours after oligonucleotide treatment.

Example 10

Analysis of Oligonucleotide Inhibition of Bcl-x Expression

Antisense modulation of bcl-x expression can be assayed in a variety of ways known in the art. For example, bcl-x mRNA levels can be quantitated by Northern blot analysis, RNAse protection assay (RPA), competitive polymerase chain reaction (PCR), or real-time PCR (RT-PCR). RNA analysis can be performed on total cellular RNA or poly(A)+ mRNA. Methods of RNA isolation are taught in, for example, Ausubel, et al., Current Protocols in Molecular Biology, Volume 1, John Wiley & Sons, Inc., 1993, pp. 4.1.1–4.2.9 and 4.5.1–4.5.3. Northern blot analysis is routine in the art and is taught in, for example, Ausubel, et al., *Current Protocols in Molecular Biology*, Volume 1, John Wiley & Sons, Inc., 1996, pp. 4.2.1–4.2.9. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

Bcl-x protein levels can be quantitated in a variety of ways well known in the art, such as immunoprecipitation, Western blot analysis (immunoblotting), ELISA, flow cytometry or fluorescence-activated cell sorting (FACS). Antibodies directed to bcl-x can be identified and obtained from a variety of sources, such as PharMingen Inc., San Diego, Calif., or can be prepared via conventional antibody generation methods. Methods for preparation of polyclonal antisera are taught in, for example, Ausubel, et al., *Current Protocols in Molecular Biology*, Volume 2, John Wiley & Sons, Inc., 1997, pp. 11.12.1–11.12.9. Preparation of monoclonal antibodies is taught in, for example, Ausubel, et al., *Current Protocols in Molecular Biology, Volume 2*, John Wiley & Sons, Inc., 1997, pp. 11.4.1–11.11.5.

Immunoprecipitation methods are standard in the art and can be found at, for example, Ausubel, et al., *Current Protocols in Molecular Biology*, Volume 2, John Wiley & Sons, Inc., 1998, pp. 10.16.1–10.16.11. Western blot (immunoblot) analysis is standard in the art and can be found at, for example, Ausubel, et al., *Current Protocols in Molecular Biology*, Volume 2, John Wiley & Sons, Inc., 1997, pp. 10.8.1–10.8.21. Enzyme-linked immunosorbent assays (ELISA) are standard in the art and can be found at, for example, Ausubel, et al., *Current Protocols in Molecular Biology*, Volume 2, John Wiley & Sons, Inc., 1991, pp. 11.2.1–11.2.22.

Example 11

Poly(A)+ mRNA Isolation

Poly(A)+ mRNA is isolated according to Miura et al., *Clin. Chem.*, 1996, 42, 1758–1764. Other methods for poly(A)+ mRNA isolation are taught in, for example, Ausubel, et al., *Current Protocols in Molecular Biology*, Volume 1, John Wiley & Sons, Inc., 1993, pp. 4.5.1–4.5.3. Briefly, for cells grown on 96-well plates, growth medium is removed from the cells and each well is washed with 200 µL cold PBS. 60 µL lysis buffer (10 mM Tris-HC1, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine, Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C. is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Example 12

Total RNA Isolation

Total mRNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 100 µL Buffer RLT is added to each well and the plate vigorously agitated for 20 seconds. 100 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 15 seconds. 1 mL of Buffer RW1 is added to each well of the RNEASY 96™ plate and the vacuum again applied for 15 seconds. 1 mL of Buffer RPE is then added to each well of the RNEASY 96™ plate and the vacuum applied for a period of 15 seconds. The Buffer RPE wash is then repeated and the vacuum is applied for an additional 10 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 60 µL water into each well, incubating 1 minute, and then applying the vacuum for 30 seconds. The elution step is repeated with an additional 60 µL water.

Example 13

Real-time Quantitative PCR Analysis of Bcl-x mRNA Levels

Quantitation of bcl-x mRNA levels is determined by real-time quantitative PCR using the ABI PRISM™ 7700

Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents are obtained from PE-Applied Biosystems, Foster City, Calif. RT-PCR reactions are carried out by adding 25 µL PCR cocktail (1x TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLI-TAQ GOLD™, and 12.5 Units MuLV reverse transcriptase) to 96 well plates containing 25 µL poly(A) mRNA solution. The RT reaction is carried out by incubation for 30 minutes at 48° C. Following a 10 minute incubation at 95° C. to activate the AMPLITAQ GOLDT™, 40 cycles of a two-step PCR protocol are carried out: 95° C. for 15 seconds (denaturation) followed by 60° C. for 1.5 minutes (annealing/extension). Bcl-x probes and primers are designed to hybridize to the human bcl-x nucleic acid sequence, using published sequence information (Boise et al., Cell, 1993, 74:597–608; GenBank accession number L20121;locus name HSBCLXL), incorporated herein as SEQ ID NO: 1.

Example 14

Northern Blot Analysis of Bcl-x mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.).

Membranes were probed using QUICKHYB™ hybridization solution (Stratagene, La Jolla, Calif.) using manufacturer's recommendations for stringent conditions with an 822-base pair bcl-x specific probe prepared by PCR from bases 33–855 of human bcl-xl sequence (Boise et al., 1993, Cell 74:597–608; GenBank accession no. L20121). To normalize for variations in loading and transfer efficiency membranes were stripped and probed for glyceraldehyde-3-phosphate dehydrogenase (GAPDH) RNA (Clontech, Palo Alto, Calif.). Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

RNAse Protection Assay For Analysis of mRNA Levels

The ribonuclease (RNase) protection assay is a sensitive and specific method for quantitating expression levels (Zinn, et al., Cell, 1983, 34:865–79). The method is based on the hybridization of a target RNA to an in vitro transcribed $^{32}$P-labeled anti-sense RNA probe from a DNA template. RNase treatment follows, resulting in degradation of single-stranded RNA and excess probe. The probe and target RNA are resolved by denaturing polyacrylamide gel electrophoresis with the "protected" probe visualized using autoradiography or beta imaging equipment. Template sets can be purchased (PharMingen Inc., San Diego Calif.) which contain a series of biologically relevant templates, each of distinct length and each representing a sequence in a distinct mRNA species. Each template set is capable of detecting up to 11 unique gene messages in a single reaction mix in addition to one or more housekeeping genes, L32 and GAPDH, which serve as internal controls. These template sets allow for multiple determinations to be made from a single sample. Multi-probe RPA can be performed on total RNA preparations derived by standard methods, without further purification of poly-A+ RNA.

Oligonucleotides were evaluated for their respective 10 effects on bcl-xs and bcl-xl mRNA levels along with total bcl-x mRNA levels, using the RIBOQUANT™ RNase protection kit (Pharmingen, San Diego Calif.). All assays were performed according to manufacturer's protocols. Briefly, multi-probe DNA template sets were used to generate antisense RNA transcripts radiolabeled with dUTP-$^{32}$P. The template set used for apoptosis genes was the human hAPO-2 set. These radiolabeled probes were hybridized overnight with typically 10 μg of total cellular RNA. The reaction mixture was then digested with single-strand RNases to generate the protected fragments which were electrophoresed through a 5% acrylamide/urea gel. Protected bands were visualized and quantitated using a PhosphorImager (Molecular Dynamics, Sunnyvale, Calif.).

Example 16

Antisense Inhibition of Bcl-x Expression-Phosphorothioate Oligodeoxynucleotides In accordance with the present invention, a series of oligonucleotides were designed to target different regions of human bcl-x RNA, using published sequences (Boise, L. H., et al., Cell, 1993, 74, 597–608; Genbank Accession No. L20121,also listed as Genbank Accession No. Z23115; locus name "HSBCLXL," incorporated herein as SEQ ID NO: 1). The oligonucleotides are shown in Table 1. Target sites are indicated by nucleotide numbers, as given in the sequence source reference (Genbank Accession No. L20121) to which the oligonucleotide binds. All compounds in Table 1 are oligodeoxynucleotides with phosphorothioate backbones (internucleoside linkages) throughout.

TABLE 1

Human bcl-x Phosphorothioate Oligodeoxynucleotides

| ISIS NO. | NUCLEOTIDE SEQUENCE[1] (5' -> 3') | SEQ ID NO: | TARGET SITE[2] | TARGET REGION |
|---|---|---|---|---|
| 11219 | CGGGTTCTCCTGGTGGCAAT | 3 | 0907–0926 | 3'-UTR |
| 11220 | CAGTGTCTGGTCATTTCCGA | 4 | 0827–0846 | Stop |
| 11221 | AGCCCAGCAGAACCACGCCG | 5 | 0797–0816 | Coding, Exon 2 |
| 11222 | GTTGAAGCGTTCCTGGCCCT | 6 | 0748–0767 | Coding, Exon 2 |
| 11223 | CAGTGCCCCGCCGAAGGAGA | 7 | 0565–0584 | Coding, Exon 1L[3] |
| 11224 | TCGCCTGCCTCCCTCAGCGC | 8 | 0399–0418 | Coding, Exon 1 |
| 11225 | CAGTGGCTCCATTCACCGCG | 9 | 0323–0342 | Coding, Exon 1 |
| 11226 | ATTCAGTCCCTTCTGGGGCC | 10 | 0242–0261 | Coding, Exon 1 |
| 11227 | AAAGTCAACCACCAGCTCCC | 11 | 0151–0170 | Coding, Exon 1 |
| 11228 | CCGGTTGCTCTGAGACATTT | 12 | 0133–0152 | AUG |
| 11229 | ACCAGTCCATTGTCCAAAAC | 13 | 0093–0112 | 5'-UTR |
| 11230 | GAAGGGAGAGAAAGAGATTC | 14 | 0001–0020 | 5'-UTR |
| 11993 | TCATTCACTACCTGTTCAAA | 15 | 0501–0520 | Coding, Exon 1 |
| 12102 | AGCCCACCAGAAGGACCCCG | 16 | scrambled 11121 | |
| 12103 | CAGTGGCTCTCACCGCATCG | 17 | scrambled 11225 | |
| 12104 | CAGCCCGCCTGCGAAGGAGA | 18 | scrambled 11223 | |
| 12105 | AGCGCAGAACCACCACGCCG | 19 | scrambled 11221 | |

[1]All linkages are phosphorothioate linkages.
[2]Coordinates from Genbank Accession No. L20121, locus name "HSBCLXL,"SEQ ID NO. 1.
[3]Where Exon 1L is indicated, the oligonucleotide targets the long but not the short mRNA transcript of bcl-x.

Oligonucleotides were tested by Northern blot analysis as described in Example 145. Oligonucleotides were tested in A549 cells at a concentration of 400 nM. The results are shown in Table 2:

TABLE 2

Effect of Antisense Phosphorothioate Oligodeoxynucleotides Targeted to Human Bcl-x on Bcl-x mRNA Levels

| ISIS NO. | SEQ ID NO: | TARGET REGION | % CONTROL | % INHIB |
|---|---|---|---|---|
| 11219 | 3 | 3'-UTR | 6 | 94 |
| 11220 | 4 | Stop | 12 | 88 |
| 11221 | 5 | Coding, Exon 2 | 11 | 89 |
| 11222 | 6 | Coding, Exon 2 | 35 | 65 |
| 11223 | 7 | Coding, Exon 1L | 9 | 91 |
| 11224 | 8 | Coding, Exon 1 | 6 | 94 |
| 11225 | 9 | Coding, Exon 1 | 25 | 75 |

TABLE 2-continued

Effect of Antisense Phosphorothioate Oligodeoxynucleotides
Targeted to Human Bcl-x on Bcl-x mRNA Levels

| ISIS NO. | SEQ ID NO: | TARGET REGION | % CONTROL | % INHIB |
|---|---|---|---|---|
| 11226 | 10 | Coding, Exon 1 | 34 | 66 |
| 11227 | 11 | Coding, Exon 1 | 10 | 90 |
| 11228 | 12 | AUG | 31 | 69 |
| 11229 | 13 | 5'-UTR | 60 | 40 |
| 11230 | 14 | 5'-UTR | 135 | — |
| 11993 | 15 | Coding, Exon 1 | 142 | — |

SEQ ID NOs 3, 4, 5, 6, 7, 8, 9, 10, 11 and 12 inhibited bcl-x mRNA levels by greater than 50%. Of these, SEQ ID Nos 3, 4, 5, 7, 8 and 11 inhibited bcl-x MRNA levels by greater than 85%.

Example 17

Dose Response Analysis of ISIS 11219 (SEQ ID NO: 3) and ISIS 11224 (SEQ ID NO: 8)

Dose-response experiments were done to quantitate bcl-x mRNA levels in A549 cells by Northern blot analysis after oligonucleotide treatment with ISIS 11219 and 11224. The IC$_{50}$s obtained for these compounds were approximately 250 nM and 175 nM, respectively.

Example 18

Antisense Inhibition of Bcl-x Expression-Phosphorothioate 2'-MOE Gapmer Oligonucleotides A second series of oligonucleotides targeted to human bcl-x was synthesized. The oligonucleotide sequences are shown in Table 3. Target sites are indicated by nucleotide numbers, as given in the sequence source reference (Genbank Accession No. L20121), to which the oligonucleotide binds.

All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. Cytidine residues in the 2'-MOE wings are 5-methylcytidines.

TABLE 3

Nucleotide Sequences of Human Bcl-x Chimeric Oligonucleotides

| ISIS NO. | NUCLEOTIDE SEQUENCE[1] (5' -> 3') | SEQ ID NO: | TARGET SITE[2] | TARGET REGION |
|---|---|---|---|---|
| 15998 | TAATAGGGATGGGCTCAACC | 20 | 0110–0129 | 5'-UTR |
| 15999 | TCCCGGTTGCTCTGAGACAT | 21 | 0135–0154 | AUG |
| 16000 | GGGCCTCAGTCCTGTTCTCT | 22 | 0227–0246 | Coding, Exon 1 |
| 16001 | TCCATCTCCGATTCAGTCCC | 23 | 0252–0271 | Coding, Exon 1 |
| 16002 | AGGTGCCAGGATGGGTTGCC | 24 | 0291–0310 | Coding, Exon 1 |
| 16003 | AGTGGCTCCATTCACCGCGG | 25 | 0322–0341 | Coding, Exon 1 |
| 16004 | CTTGCTTTACTGCTGCCATG | 26 | 0380–0399 | Coding, Exon 1 |
| 16005 | GCCGGTACCGCAGTTCAAAC | 27 | 0422–0441 | Coding, Exon 1 |
| 16006 | CTGTTCAAAGCTCTGATATG | 28 | 0490–0509 | Coding, Exon 1 |
| 16007 | TACCCCATCCCGGAAGAGTT | 29 | 0520–0539 | Coding, Exon 1L |
| 16008 | AAAGGCCACAATGCGACCCC | 30 | 0544–0563 | Coding, Exon 1L |
| 16009 | CTACGCTTTCCACGCACAGT | 31 | 0581–0600 | Coding, Exon 1L |
| 16010 | TCCAAGCTGCGATCCGACTC | 32 | 0623–0642 | Coding, Exon 1L |
| 16011 | CTGGATCCAAGGCTCTAGGT | 33 | 0664–0683 | Coding, Exon 1L |
| 16012 | CCAGCCGCCGTTCTCCTGGA | 34 | 0679–0698 | Coding, Exon 1L 3' end |
| 16013 | TAGAGTTCCACAAAAGTATC | 35 | 0699–0718 | Coding, Exon 2 5' end |
| 16014 | AGCGTTCCTGGCCCTTTCGG | 36 | 0743–0762 | Coding, Exon 2 |
| 16015 | GTCATGCCCGTCAGGAACCA | 37 | 0771–0790 | Coding, Exon 2 |
| 16016 | TGAGCCCAGCAGAACCACGC | 38 | 0799–0818 | Coding, Exon 2 |
| 16017 | CAGTGTCTGGTCATTTCCGA | 3 | 0827–0846 | Stop |

TABLE 3-continued

Nucleotide Sequences of Human Bcl-x Chimeric Oligonucleotides

| ISIS NO. | NUCLEOTIDE SEQUENCE[1] (5' -> 3') | SEQ ID NO: | TARGET SITE[2] | TARGET REGION |
|---|---|---|---|---|
| 16018 | GAGGGTAGAGTGGATGGTCA | 39 | 0845–0864 | 3'-UTR |
| 16019 | GGAGGATGTGGTGGAGCAGA | 40 | 0876–0895 | 3'-UTR |
| 16020 | CGGGTTCTCCTGGTGGCAAT | 2 | 0907–0926 | 3'-UTR |

[1]Emboldened residues, 2'-MOE residues (others are 2'-deoxy-). 2'-MOE cytosines are 5-methyl-cytosines; all linkages are phosphorothioate linkages.
[2]Coordinates from Genbank Accession No. L20121, locus name "HSBCLXL," SEQ ID NO. 1.

Oligonucleotides were tested by Northern blot analysis as described in Example 14. Chimeric oligonucleotides were tested in A549 cells at a concentration of 200 nM. Results are shown in Table 4. Where present, "N.D." indicates "not determined".

TABLE 4

Effect of Chimeric Antisense Oligonucleotides Targeted to Human Bcl-x on Bcl-x mRNA Levels

| ISIS NO. | SEQ ID NO: | TARGET REGION | % CONTROL | % INHIB |
|---|---|---|---|---|
| 15998 | 20 | 5'-UTR | 13 | 87 |
| 15999 | 21 | AUG | 4 | 96 |
| 16000 | 22 | Coding, Exon 1 | 4 | 96 |
| 16001 | 23 | Coding, Exon 1 | 17 | 83 |
| 16002 | 24 | Coding, Exon 1 | 8 | 92 |
| 16003 | 25 | Coding, Exon 1 | 12 | 88 |
| 16004 | 26 | Coding, Exon 1 | 5 | 95 |
| 16005 | 27 | Coding, Exon 1 | 17 | 83 |
| 16006 | 28 | Coding, Exon 1 | 28 | 72 |
| 16007 | 29 | Coding, Exon 1L | 31 | 69 |
| 16008 | 30 | Coding, Exon 1L | N.D. | N.D. |
| 16009 | 31 | Coding, Exon 1L | 3 | 97 |
| 16010 | 32 | Coding, Exon 1L | 13 | 87 |
| 16011 | 33 | Coding, Exon 1L | 31 | 69 |
| 16012 | 34 | Coding, Exon 1L 3' end | 30 | 70 |
| 16013 | 35 | Coding, Exon 2 5' end | 85 | 15 |
| 16014 | 36 | Coding, Exon 2 | 22 | 78 |
| 16015 | 37 | Coding, Exon 2 | 12 | 88 |
| 16016 | 38 | Coding, Exon 2 | 28 | 72 |
| 16017 | 3 | Stop | 18 | 82 |
| 16018 | 39 | 3'-UTR | 40 | 60 |
| 16019 | 40 | 3'-UTR | 40 | 60 |
| 16020 | 2 | 3'-UTR | 20 | 80 |

Of the chimeric oligonucleotides tested, all but SEQ ID NO: 35 inhibited bcl-x mRNA levels by at least 60%. Of these, SEQ ID NOS 20–27, 31, 32, 37, 3 and 2 reduced bcl-x mRNA levels by 80% or more.

Example 19

Dose-response Effect of ISIS 15999 and Mismatches on Bcl-x mRNA Levels in A549 Cells Dose-response experiments were done to quantitate bcl-x mRNA levels in A549 cells by Northern blotting after oligonucleotide treatment with ISIS 15999 and compounds based on the ISIS 15999 sequences but with 2, 4, 6 or 8 mismatches from the 15999 sequence. The $IC_{50}$ obtained for ISIS 15999 was estimated to be well below 25 nM because the lowest oligonucleotide dose tested, 25 nM, gave approximately 70% reduction of bcl-x mRNA levels and oligonucleotide doses of 50 nM to 200 nM gave inhibition of greater than 90%, with nearly complete ablation of bcl-x mRNA at the highest dose. Oligonucleotides with 2 or 4 mismatches had $IC_{50}$s of approximately 200 nM, the highest dose tested, and oligonucleotides with 6 or 8 mismatches did not inhibit mRNA levels below control levels.

Example 20

Dose-response Effect of ISIS 16009 and Mismatches on Bcl-x mRNA Levels in A549 Cells Dose-response experiments were done to quantitate bcl-x mRNA levels in A549 cells by Northern blot analysis after oligonucleotide treatment with ISIS 16009 and compounds based on the ISIS 16009 sequence but with 2, 4, 6 or 8 mismatches from the 16009 sequence. The $IC_{50}$ obtained for ISIS 16009 was estimated to be 40–50 nM. $IC_{50}$s could not be obtained for mismatched oligonucleotides because 50% inhibition of mRNA levels was not achieved at any of the doses tested (25–200 nM).

Example 21

Optimization of ISIS 15999 and 16009

Several analogs of ISIS 15999 (SEQ ID NO: 21) and ISIS 16009 (SEQ ID NO: 31) were prepared. These had various placements of 2'-O-methoxyethyl ($2^1$-MOE) modifications and either uniformly phosphorothioate (P=S) backbones or chimeric backbones in which the 2'-O-methoxyethyl wings had phosphodiester (P=O) backbones and the deoxy gap had a phosphorothioate (P=S) backbone. These compounds are shown in Table 5. All 2'-MOE cytosines were 5-methyl-cytosines (5-meC).

TABLE 5

Analogs of ISIS 15999 and 16009

| ISIS No. | SEQUENCE[1] | SEQ ID NO: |
|---|---|---|
| 15999 | TsCsCsCsGsGsTsTsGsCsTsCsTsGsAsGsAsCsAsT | 21 |
| 17791 | ToCoCoCoGsGsTsTsGsCsTsCsTsGsAsGoAoCoAoT | 21 |
| 17958 | TsCsCsCsGsGsTsTsGsCsTsCsTsGsAsGsAsCsAsT | 21 |
| 17959 | TsCsCsCsGsGsTsTsGsCsTsCsTsGsAsGsAsCsAsT | 21 |
| 16009 | CsTsAsCsGsCsTsTsTsCsCsAsCsGsCsAsCsAsGsT | 31 |
| 17792 | CoToAoCoGsCsTsTsTsCsCsAsCsGsCsAoCoAoGoT | 31 |
| 17956 | CsTsAsCsGsCsTsTsTsCsCsAsCsGsCsAsCsAsGsT | 31 |
| 17957 | CsTsAsCsGsCsTsTsTsCsCsAsCsGsCsAsCsAsGsT | 31 |
| 17619 | CsTsAsCsGsCsTsTsTsCsCsAsCsGsCsAsCsAsGsT | 31 |

[1] Emboldened residues are 2'-MOE residues (others are 2'-deoxy). All 2'-MOE cytosines were 5-methylcytosines; linkages are indicated as "s" for phosphorothioate (P = S) linkages and "o" for phosphodiester (P = O) linkages.

Example 22

Dose-response Effect of ISIS 16009 and Analogs on Bcl-x mRNA Levels in A549 Cells Dose-response experiments were done to quantitate bcl-x mRNA levels in A549 cells by Northern blot analysis after oligonucleotide treatment with ISIS 16009 and analogs shown in Table 5. Oligonucleotides were tested at concentrations of 50, 100, 150 and 200 nM. $IC_{50}$s obtained are shown in Table 6. An $IC_{50}$ was not obtained for ISIS 17619 (P=S, full deoxy) because 50% reduction in bcl-x mRNA was not achieved at doses up to 200 nM.

TABLE 6

$IC_{50}$s for analogs of SEQ ID NO: 31

| ISIS No. | SEQUENCE | $IC_{50}$ (nM) |
|---|---|---|
| 16009 | CsTsAsCsGsCsTsTsTsCsCsAsCsGsCsAsCsAsGsT | 35 |
| 17792 | CoToAoCoGsCsTsTsTsCsCsAsCsGsCsAoCoAOGoT | 143 |
| 17956 | CsTsAsCsGsCsTsTsTsCsCsAsCsGsCsAsCsAsGsT | 47 |
| 17957 | CsTsAsCsGsCsTsTsTsCsCsAsCsGsCsAsCsAsGsT | 43 |
| 17619 | CsTsAsCsGsCsTsTsTsCsCsAsCsGsCsAsCsAsGsT | >200 |

Example 23

Western Blot Analysis of Bcl-x Protein Levels

Western blot analysis (immunoblot analysis) was carried out using standard methods. Generally, cells were harvested 16–20 hours after oligonucleotide treatment, washed once with PBS, suspended in Laemmli buffer (100 ul/well), boiled for 5 minutes and loaded on a 16% SDS-PAGE gel. Gels were run for 1.5 hours at 150 V, and transferred to membrane for western blotting. Appropriate primary antibody directed to bcl-x was used, with a radiolabelled or fluorescently labeled secondary antibody directed against the primary antibody species. Bands were visualized using a PHOSPHORIMAGER™ (Molecular Dynamics, Sunnyvale, Calif.).

ISIS 15999 and 16009 were tested for the ability to reduce bcl-x protein levels in A549. Both compounds were found to reduce bcl-x protein levels in a dose-dependent manner.

Example 24

Effect of ISIS 15999 on Bcl-x Protein Levels in SEM-K2 Cells

SEM-K2 is a human cell line derived from a patient suffering from a t(4;11) acute lymphoblastic leukemia. Pocock, C. F. E. et al., Br. J. Haematol. (1995), 90(4), 855–67. SEM-K2 cells in exponential phase of growth were maintained in RPMI 1460 medium (Life Technologies, Inc., Gaithersburg, Md.) supplemented with 10% fetal bovine serum, 2 mM glutamine and penicillin/streptomycin, at 37° C. in 5%$CO_2$/95% air. Cells were transferred in 1 mL volumes at approximately 1–5×10⁶ cells/ml to 24-well plates. After one hour, 10 μM of ISIS 15999 or scrambled control 15691 (GACATCCCTTTCCCCCTCGG; SEQ ID No. 41) was added to wells, without cationic lipid. At 24 hours and 48 hours repeat doses of 5 μM oligonucleotide were added. Cells were analyzed at 72 hours.

For Western blot and flow cytometric protein analysis, cells were washed once in phosphate-buffered saline and pelleted by centrifugation at 1200 rpm for 5 minutes, and resuspended in cell lysis buffer (5M NaCl, 0.1 M HEPES, 500 mM sucrose, 0.5M EDTA, 100 mM spermine, 1 mg/ml aprotinin, 10% Triton X-100) for 15 minutes on ice. Total protein was quantified spectrophotometrically (BioRad) and 100 μg lysate was loaded onto 15% polyacrylamide gels and run at 200V for 45 minutes. Following protein transfer to nitrocellulose membrane, blots were immunostained with mouse monoclonal bcl-x antibody (Transduction Laboratories, Lexington, Ky.) followed by horseradish peroxidase-conjugated goat anti-mouse secondary antibody (Santa Cruz Biotechnology, Inc., Santa Cruz, Calif.). Protein was qualitatively visualized by ECL (Amersham, Piscataway, N.J.) and exposure on photographic film. Cells for flow cytometry were permeabilized by fixation on ice in 70% ethanol for 30 minutes. Two-step immunostaining employed bcl-xl antibody (Jackson ImmunoResearch Lab., Westr Grove, Pa.) followed by fluorescein isothiocyanate (FITC)-conjugated anti-mouse antibody. Cells were analyzed using a FACScalibur™ running Cellquest software (Becton Dickinson, Franklin Lakes, N.J.). A lymphoid-enriched gate was used for acquisition of 50,000 events. Fluorescence detector 1 was used with logarithmic amplification for detection of FITC fluorescence.

Median fluorescence intensity of bcl-x-stained SEM-K2 cells was measured using WINMIDI 2.5 software. SEM-K2 express bcl-x at relatively high levels as detected by immunofluorescence. Median fluorescence intensity for the population treated with 10 μM ISIS 15999 was compared with positive and negative control samples, respectively, and the percentage reduction in bcl-x expression was calculated. Using 10 μM ISIS 15999, 50% reduction in bcl-x was measured at 48 hours after initial treatment.

Example 25

SCID-human Leukemia Model and In Vivo Bcl-xl Antisense Treatment $10^7$ SEM-K2 cells in exponential phase of growth were injected subcutaneously into 8 SCID-NOD mice as a bolus (suspended in sterile saline). Engraftment and tumor formation occurred over a 2–3 week period. Micro Alzet pumps (Alza, Newark, Del.) capable of delivering a continuous subcutaneous infusion over 14 days were used to deliver a dose of 100 pg per day (equivalent to 5 mg/kg) of ISIS 16009 and scrambled control ISIS 15691 into two groups of three animals, respectively. The remaining two animals received vehicle (sterile saline) only.

The expression of bcl-x measured in SEM-K2 cells from SCID-hu xenografts was shown to be dramatically reduced by 14-day infusion of 5 mg/kg/day equivalent (100 μg/day) of ISIS 16009. Mean reductions in expression of approximately 90% (n=3) compared to control (p<0.01) were measured using quantitative flow cytometry. This was compared to statistically insignificant (<20%, p<0.3) reductions in bcl-x expression by scrambled control oligonucleotide ISIS 15691 (n=3).

Example 26

Stimulation and Measurement of Apoptosis

Xenografts were removed after sacrifice and mechanically dispersed into large volumes of medium. Leukocytes were purified by density gradient centrifugation and washed with medium before resuspending in 1 ml volumes at $1-5 \times 10^6$ cells/ml. Cells were incubated at 37° C. in 95% humidified air/5% $CO_2$ for 2 hours prior to induction of apoptosis with 20 μg/ml VP-16 (Etoposide) over 24 hours. Each xenograft cell suspension treated with VP-16 was paired with a respective negative control. Apoptosis was assessed nonspecifically using quantification of light scatter changes; reduction in side scatter (due to chromatin condensation) and reduction in forward scatter (due to cell shrinkage) are early changes associated with apoptosis. Bimodal population distributions consisting of apoptotic and non-apoptotic cells could be measured respectively allowing estimation of an apoptotic index for treated and negative control. Fold increase in apoptosis was calculated from their ratio. More specific determination of apoptosis was achieved using the Apo-Alert Caspase-3 Colorimetric Assay Kit (Clontech, Palo Alto, Calif.). This is a DEVD-specific caspase assay, a quantitative assay for the activity of caspase-3, a member of the caspase family thought to mediate apoptosis in most mammalian cell types. This assay utilizes a synthetic tetrapeptide, Asp-Glu-Val-Asp (DEVD; SEQ ID No. 42), labeled with either a fluorescent mol., 7-amino-4-trifluoromethyl coumarin (AFC), or a calorimetric mol., p-nitroanilide (pNA) as substrates. DEVD-dependent protease activity is assessed by detection of the free AFC or pNA cleaved from the substrates. Cell lysates were incubated with DEVD conjugated to paranitroanilide, a calorimetric substrate cleaved by CPP32 (caspase-3) and detectable using calorimetric spectrophotometry at 405 nm. The fold increase in $OD_{405nm}$ was used to determine the net VP-16-induced apoptosis.

Sequence specific increases in CPP32 activation measured by DEVD-paranitroanilide cleavage were detected. A 46% increase in $OD_{405nm}$ was detected above control xenografts for ISIS 16009-treated SCID-hu models (n=3). Scrambled control oligonucleotide-treated xenografts yielded very little change in VP-16-induced apoptosis (n=3) which was quantitively similar to that of xenografts not treated with oligonucleotide. A scatter plot of bcl-x expression versus fold increase in CPP32 activity (pooled from all 8 animals) revealed a positive correlation ($r_s$>8) suggesting a definite relationship between bcl-x expression and apoptosis sensitivity to VP-16. A similar profile of change was detected in light scatter measurements of apoptosis. Sequence-specific increase in apoptotic index was associated with ISIS 16009; this was not seen in the ISIS 15691 (control) treated group nor the untreated control group. Again, a pooled scatter plot shows a positive correlation ($r_s$>8) for bcl-x versus apoptosis (light scatter), suggesting a strong relationship.

Example 27

Measurements of Cell Viability and Clonogenicity

Propidium iodide (20 μg/ml) was added to PBS-washed cells and flow cytometry was performed using fluorescence detector 3 vs. side scatter. This charged dye is excluded from live cells and may be used to detect dead or late apoptotic cells in which propidium iodide readily becomes incorporated. Viable and non-viable cells were counted and a viability fraction was computed. The ratio of VP-16 to negative control viability was determined to provide a measure of VP-16-induced reduction in viability. Viable cells metabolize (reduce) the tetrazolium salt MTT (Roche Molecular Biochemicals, Indianapolis, Ind.) to a purple formozan product which is detectable by spectophotometry, thus providing a means for quantitation. The fold decrease in cell viability was determined at 96 hours. Cell proliferation increases MTT metabolizing capacity in vitro, thus providing an index of clonogenic growth. The fold reduction in VP-16-treated versus negative control cells was determined to provide a measure of net cytotoxic effect on clonogenicity.

A reduction in MTT viability was observed and shown to be sequence-specific. A pooled scatter plot (n=8) of bcl-x expression versus fold decrease in metabolic viability shows a negative correlation ($r_s$=−5) is seen, which is consistent with a role of bcl-x in providing a survival advantage in cells stimulated to undergo apoptosis by VP-16.

Example 28

Effect of Antisense Oligonucleotides On Expression of Bcl-xs and Bcl-xl Transcripts Additional oligonucleotides were designed to target particular areas of exon 1 and exon 2 of human bcl-x, particularly around the exon 1/exon 2 splice site and in sequence regions present in bcl-xl but not in bcl-xs. These oligonucleotides are shown in Table 7. All backbone linkages are phosphorothioates; All 2'MOE cytosines are 5-methylcytosines.

TABLE 7

Oligonucleotides targeted to exon1/exon 2 of human bcl-x

| ISIS # | Sequence | Target Region | Target site | SEQ ID NO: |
|---|---|---|---|---|
| 16009 | CTACGCTTTCCACGCACAGT | Coding, Exon 1L | 581–600 | 31 |
| 16968 | CTCCGATGTCCCCTCAAAGT | 6 base mismatch | 16009 | 43 |
| 15999 | TCCCGGTTGCTCTGAGACAT | AUG | 135–154 | 21 |
| 16972 | TCACGTTGGCGCTTAGCCAT | 6 base mismatch | 15999 | 44 |
| 16011 | CTGGATCCAAGGCTCTAGGT | Coding, Exon 1L | 664–683 | 33 |
| 22783 | CTGGATCCAAGGCTCTAGGT | Coding, Exon 1L | 664–683 | 33 |
| 16012 | CCAGCCGCCGTTCTCCTGGA | Coding, Exon 1L 3' end | 679–698 | 34 |
| 22784 | CCAGCCGCCGTTCTCCTGGA | Coding, Exon 1L 3' end | 679–698 | 34 |
| 16013 | TAGAGTTCCACAAAAGTATC | Coding, Exon 2 5' end | 699–718 | 35 |
| 22781 | TAGAGTTCCACAAAAGTATC | Coding, Exon 2 5' end | 699–718 | 35 |
| 22782 | CAAAAGTATCCCAGCCGCCG | Coding, Exon 1/2 splice | 689–708 | 45 |
| 22785 | GCCGCCGTTCTCCTGGATCC | Coding, Exon 1L | 676–695 | 46 |
| 23172 | GTTCCTGGCCCTTTCGGCTC | Coding, Exon 2 | 740–759 | 47 |
| 23173 | CAGGAACCAGCGGTTGAAGC | Coding, Exon 2 | 760–779 | 48 |
| 23174 | CCGGCCACAGTCATGCCCGT | Coding, Exon 2 | 780–799 | 49 |
| 23175 | TGTAGCCCAGCAGAACCACG | Coding, Exon 2 | 800–819 | 50 |

Human bcl-x has two forms, a long form known as bcl-xl and a short form known as bcl-xs. These result from alternatively spliced MRNA transcripts. The protein of bcl-xl is similar in size and structure to bcl-2, and could inhibit cell death upon growth factor withdrawal. The protein of bcl-xs is 63 amino acids shorter than bcl-xl. It could inhibit the bcl-2 function, thus promoting programmed cell death (apoptosis). Oligonucleotides were evaluated for their respective effects on bcl-xs and bcl-xl MRNA levels along with total bcl-x mRNA levels, using the RIBOQUANT™ RNase protection kit (Pharmingen, San Diego, Calif.). All assays were performed according to manufacturer's protocols. Results are shown in Table 8.

TABLE 8

Effect of antisense oligonucleotides on bcl-xs and bcl-xl

| ISIS # | SEQ ID NO | % CONTROL bcl-xs | % CONTROL bcl-xl | % CONTROL total bcl-x | bcl-xs/ bcl-xl (%) | bcl-xs/ bcl-xl* |
|---|---|---|---|---|---|---|
| no oligo | — | 100 | 100 | 100 | 17.56 | 1 |
| 16009 | 31 | 20 | 24 | 24 | 12.45 | 0.71 |
| 16968 | 43 | 20 | 15 | 21 | 20.18 | 1.15 |
| 15999 | 21 | ND** | ND | ND | — | — |
| 16972 | 44 | 60 | 91 | 87 | 11.68 | 0.67 |
| 16011 | 33 | ND | ND | ND | — | — |
| 22783 | 33 | 620 | 35 | 120 | 293.10 | 16.69 |
| 16012 | 34 | 48 | 63 | 61 | 13.17 | 0.75 |
| 22784 | 34 | 204 | 72 | 92 | 48.63 | 2.77 |
| 16013 | 35 | 60 | 83 | 82 | 12.46 | 0.71 |
| 22781 | 35 | ND | ND | ND | — | — |
| 22782 | 45 | 64 | 76 | 75 | 15.72 | 0.89 |
| 22785 | 46 | 248 | 53 | 83 | 80.14 | 4.56 |
| 23172 | 47 | 84 | 77 | 79 | 19.38 | 1.10 |
| 23173 | 48 | ND | ND | ND | — | — |
| 23174 | 49 | 56 | 67 | 66 | 14.93 | 0.85 |
| 23175 | 50 | 52 | 82 | 78 | 11.44 | 0.65 |

* In control cells without oligonucleotide, the bcl-xs/bcl-xl mRNA ratio is 17.56. This column gives the change from this number (i.e, where the bcl-xs/bcl-xl mRNA ratio is 17.56, this column reads "1").
** where "ND" is present, the RNA on the gel could not be quantitated.

ISIS 22783, a fully 2'-MOE, fully-phosphorothioate oligonucleotide targeted to exon 1 of the bcl-xl transcript (not the bcl-xs transcript), is able to change the ratio of bcl-xs to bcl-xl from 17% to 293%, without reducing the total bcl-x mRNA level in A549 cells. That is, it reduced the bcl-xl form but dramatically increased the bcl-xs form.

ISIS 22783 was tested by RNAse protection assay for ability to inhibit bax, another apoptotic gene. It had no effect on bax mRNA levels. ISIS 22783 is also fully complementary to the murine bcl-x mRNA which makes it useful for animal studies.

Example 29

Antisense Redirection of Bcl-x Splice Products in Other Cell Lines

In addition to its activity in A549 cells shown in the previous examples, ISIS 22783 was able to similarly alter the bcl-xl/xs splice product ratio in human 293T embryonic kidney carcinoma cells, human C8161 melanoma cells and HeLa cells.

Example 30

Additional Mmodifications of the ISIS 22783 Sequence

It is believed that modifications which provide tight binding of the antisense compound to the target and resistance to nucleases are also particularly useful in targeting splice sites. One such modification is the 2'-methoxyethoxy (2'-MOE) modification. Other examples of such modifications include but are not limited to sugar modifications including 2'-dimethylaminooxyethoxy (2'-DMAOE) and 2'-acetamides; backbone modifications such as morpholino, MMI and PNA backbones, and base modifications such as C-5 propyne.

An antisense compound which has the ISIS 22783 sequence and a 2'-DMAOE modification on each sugar was compared to its 2'-MOE analog for ability to alter the ratio of bcl-x splice products. The results are shown in Table 9.

TABLE 9

Comparison of the 2'-MOE and 2'-DMAOE analogs of the ISIS 22783 sequence for effect on bcl-xs/bcl-xl ratio

| Chemistry | SEQ ID NO: | Oligo Concentration | Ratio (approx.) of bcl-xs/bcl-xl |
|---|---|---|---|
| 2'-MOE | 33 | 100 | 4.5 |
| " | " | 200 | 8.5 |
| " | " | 400 | 18 |
| 2'-DMAOE | " | 100 | 1.8 |
| " | " | 200 | 4 |
| " | " | 400 | 12 |

Thus compared to the 2'-MOE compound, the 2'-DMAOE compound showed qualitatively similar, though quantitatively slightly less, ability to alter the ratio of bcl-xs to bcl-xl splice products. 2'-DMAOE compounds are therefore preferred.

Preliminary experiments with a morpholino-backbone compound with the 22783 sequence showed good activity as measured by RPA. Compounds were prepared according to U.S. Pat. No. 5,034,506, and transfected into HeLa cells by scrape-loading. Summerton et al., 1997, Antisense Nucleic Acid Drug Dev., 7,63–70.

A peptide-nucleic acid (PNA) oligonucleotide having the ISIS 22783 sequence (SEQ ID NO: 33) was synthesized as described in Example 4 hereinabove. The oligonucleotide (ISIS 32262) was uniformly modified with a PNA backbone throughout. A 5-base mismatch compound (ISIS 32263, SEQ ID NO: 52) was also synthesized as a full PNA. HeLa cells were transfected with these compounds by electroporation with a 200V pulse using a BTX Electro Cell Manipulator 600 (Genetronics, San Diego, Calif.) and RNA was isolated 24 hours later. The effects of the PNA compounds on bcl-x splicing is shown in Table 10.

TABLE 10

Effect of PNA analogs of the ISIS 22783 sequence on bcl-xs/bcl-xl transcript ratio

| Chemistry | SEQ ID NO: | Oligo Concentration | Ratio (approx.) of bcl-xs/bcl-xl |
|---|---|---|---|
| No oligo | | | 1.0 |
| PNA | 33 | 1 µM | 1.5 |
| | 33 | 2 µM | 2.0 |
| | 33 | 5 µM | 3.5 |
| | 33 | 10 µM | 6.5 |
| | 33 | 15 µM | 7.75 |
| | 33 | 25 µM | 11.5 |
| PNA | 52 (control) | 1 µM | 1.5 |
| | 52 (control) | 2 µM | 0.75 |
| | 52 (control) | 5 µM | 0.75 |
| | 52 (control) | 10 µM | 1.0 |
| | 52 (control) | 15 µM | 0.75 |
| | 52 (control) | 25 µM | 1.0 |

Thus the PNA compound is also able to alter bcl-x splice products and is therefore preferred.

Example 31

Antisense Inhibition of Bcl-xl RNA and Protein in Primary Keratinocyte (skin) Cells Normal human neonatal keratinocytes (hKn) cells (Cascade Biologics, Inc., Portland, Oreg.), which are primary keratinocyte cells, were treated with ISIS 16009 and bcl-xl mRNA and protein levels were analyzed. Cells were grown in 100 mm tissue culture dishes until 70—70% confluent. Cells were transfected with oligonucleotide in the presence of cationic lipid as follows. Lipofectin™ (Gibco/BRL) was used at a concentration of 10 µg/ml Opti-MEM™ (Gibco/BRL). A 5 ml mixture of Opti-MEM™, Lipofectin™ and varying amounts of oligonucleotide was equilibrated for 30 minutes at room temperature. The cells were washed twice with Opti-MEM™ and then treated with the Opti-MEM™/Lipofectin™/oligonucleotide mixture for 4 hours. The mixture was then replaced with normal growth medium. Cells were harvested or analyzed 24 hours later at the indicated times. Antisense or scrambled oligonucleotides were transfected at concentrations of 50, 100, 200 or 300 nM. Total RNA was harvested from cells using the RNAeasy™ method (Qiagen, Valencia, Calif.). Equal amoutns of RNA (10–20 pg) were resolved in 1.2% agarose gels containing 1.1% formaldehyde and transferred overnight to nylon membranes. Membranes were probed with $^{32}$P-labeled bcl-xl, bcl-2 or G3PDH cDNAs. Radioactive probes were generated using the Strip-EZ™ kit (Ambion, Austin, Tex.) and hybridized to the membrane using QuikHyb™ solution (Stratagene, La Jolla, Calif.). The amount of RNA was quantified and normalized to G3PDH mRNA levels using a Molecular Dynamics PhosphorImager.

ISIS 15999 and 16009 showed comparable (>90%) inhibition of bcl-xl mRNA expression at a 200 nM screening dose. ISIS 16009 was found to decrease the bcl-xl mRNA in hKn cells in a concentration-dependent manner with an IC50 of approximately 50 nM. The scrambled control oligonucleotide for ISIS 16009, ISIS 20292 (CGACACGTACCTCTCGCATT; bold=2'-MOE, remainder is 2'-deoxy; backbone is phosphorothioate; SEQ ID NO:51) had no effect. The RNA expression of other apoptotic genes [AI, Bad, Bak, bcl-2, as detected by RNAse protection assay using the RiboQuant™ human Apo-2 probe set and protocol (Pharmingen, San Diego, Calif.)] or G3PDH (as detected by Northern blot analysis) was unaffected by ISIS 16009 or 15999.

It should be noted that while ISIS 16009 and 15999 hybridize to regions of the bcl-x gene that are present in both bcl-xl and bcl-xs, there is no significant expression of bcl-xs in HUVEC, hKn or A549 cells, so these compounds are considered as bcl-xl inhibitors because of the insignificant contribution of bcl-xs to the effects demonstrated.

The level of bcl-xl protein in antisense-treated hKn cells was examined by Western analysis. Whole cell extracts were prepared by lysing the cells in RIPA buffer (1x PBS, 1% NP40, 0.1% deoxycholate, 0.1% SDS, containing the complete protease inhibitor mix (Boehringer Mannheim). Protein concentration of the cell extracts was measured by Bradford assay using the BioRad kit (BioRad, Hercules, Calif.) . Equal amounts of protein (10–50 pg) were then resolved on a 10% SDS-PAGE gel (Novex, San Diego, Calif.) and transferred to PVDF membranes (Novex). The membranes were blocked for one hour in PBS containing 0.1% Tween-20 and 5% milk powder. After incubation at room temperature with a 1:500 dilution of a mouse monoclonal bcl-x antibody (Transduction Labs, Lexington, Ky.), the membranes were washed in PBS containing 0.1% Tween-20 and incubated with a 1:5000 dilution of goat anti-mouse horseradish peroxidase conjugated antibody in blocking buffer. Membranes were washed and developed using Enhanced Chemiluminescent (ECL) detection system (Amersham, Piscataway, N.J.).

24 hours after treatment, bcl-xl protein levels decreased in a concentration-dependent manner. Treatment resulted in greater than 70% inhibition of bcl-xl protein. This decrease remained low for over 48 hours after transfection.

Example 32

Ultraviolet Irradiation of A549 and hKn Cells

A549 and hKn cells were irradiated with UV-B light when they were approximately 70–80% confluent or 24 hours after treatment with oligonucleotide. Immediately before UV-B treatment, cells were washed twice with PBS and then exposed to UV-B light in a Stratalinker UV Crosslinker 1800 model (Stratagene, La Jolla, Calif.) containing 5 15-watt 312 nm bulbs. The cells were exposed to 50 mJ/m$^2$, 100 mJ/m$^2$ or 200 mJ/m$^2$ of UV-B radiation. The dose of UV-B radiation was calibrated using a UVX radiometer (UVP). Following UV irradiation, the cells were incubated in the standard medium for an additional 24 hours. Control plates for UV-B treatment were simply washed 3 times in PBS and incubated in the standard medium for an additional 24 hours. Cells were examined for apoptosis by staining the ethanol-fixed cell nuclei with propidium iodide and examining the DNA content by flow cytometry. Apoptotic cells were identified by their sub-diploid DNA content. Cells were washed twice with cold PBS and resuspended in 1 ml of 70% ethanol. After 1 hour incubation at room temperature, cells were washed in PBS and resuspended in 1 ml propidium iodide staining solution (50 μg/ml propidium iodide, 0.5 U/ml RNAse A, 2000 U/ml RNase Tl. After 30 minutes at room temperature, cell cycle analysis was performed by flow cytometry using a Becton Dickinson Calibur FACS analyzer. The fluorescence of individual nuclei of 10,000 cells was measured using a FACScan flow cytometer. Results were expressed as percentage apoptotic cells.

Example 33

Antisense Sensitization of A549 Cells to UV-induced Cell Death

A549 cells were treated with 100 nM ISIS 22783 or the 5-mismatch ISIS 26080 (CTGGTTACACGACTCCAGGT; SEQ ID NO: 52) and exposed to ultraviolet (UV) radiation. The percent apoptotic cells was quantitated by propidium iodide staining according to standard methods. Results are shown in Table 11.

TABLE 11

| Combination of ISIS 22783 and UV irradiation | | | |
|---|---|---|---|
| Compound | UV mJ/M$^2$ | % Apoptotic cells (approx) | SEQ ID NO: |
| No oligo | 0 | <1 | |
| | 50 | 1 | |
| | 100 | 10 | |
| | 200 | 22 | |
| ISIS 22783 | 0 | 2 | 33 |
| | 50 | 4 | 33 |
| | 100 | 33 | 33 |
| | 200 | 27 | 33 |
| ISIS 26080 | 0 | 1 | 52 |
| | 50 | 6 | 52 |
| | 100 | 15 | 52 |
| | 200 | 29 | 52 |

Thus the response to the apoptotic stimulus (irradiation) has been changed after antisense treatment resulting in increased apoptosis.

Example 34

Antisense Sensitization of Primary Keratinocyte Cells to UV-induced Cell Death

Exposure of skin to UV radiation and other DNA-damaging agents triggers a protective response against DNA damage. We examined the role of bcl-xl in resistance of keratinocytes to UV-B-induced apoptosis. As for A549 cells, treatment of hKn cells with ISIS 16009 sensitized the cells to apoptosis induced by UV-B irradiation. Less than 7% of cells treated with no oligonucleotide or control oligonucleotide and irradiated with 100 mJ/m² UV-B irradiation underwent apoptosis. In contrast, when the cells were transfected with 300 nM of the bcl-xl inhibitor ISIS 16009 and treated with the same dose of UV radiation, over 35% of the cells became apoptotic.

Example 35

Cisplatinum Treatment of AS49 and hKn Cells

Cisplatinum is an alkylating agent that causes DNA damage and can induce apoptosis. Gill and Windebank, 1998, J. Clin. Invest. 101:2842–2850. A549 and hKn cells were treated with cisplatinum when they were approximately 70–80% confluent or 24 hours after treatment with oligonucleotide. Cis-diamminedichloroplatinum II (Cisplatinum, Sigma, St. Louis, Mo.) was dissolved in distilled water at a concentration of 1 mg/ml, and was added to the standard medium at a dose range of 0.5 to 10 μg/ml and incubated with cells for 24 hours.

Example 36

Antisense Sensitization of A549 Cells to Cisplatinum-induced Cell Death

A549 cells were treated with 100 nM ISIS 22783 or the 5-mismatch ISIS 26080 and cisplatinum at various doses. The percent apoptotic cells was quantitated by propidium iodide staining according to standard methods. Results are shown in Table 12.

TABLE 12

Combination of ISIS 22783 and Cisplatinum

| Compound | Cisplatinum dose (μg/ml) | % Apoptotic cells (approx) | SEQ ID NO: |
|---|---|---|---|
| No oligo | 0 | 4 | |
| | 1 | 5 | |
| | 10 | 8 | |
| | 50 | 18 | |
| ISIS 22783 | 0 | 3 | 33 |
| | 1 | 6 | 33 |
| | 10 | 13 | 33 |
| | 50 | 27 | 33 |
| ISIS 26080 | 0 | 3 | 52 |
| | 1 | 2 | 52 |
| | 10 | 7 | 52 |
| | 50 | 21 | 52 |

Thus the cells have been sensitized to the apoptotic stimulus (in this case a cytotoxic chemotherapeutic drug) after antisense treatment resulting in increased apoptosis.

Example 37

Antisense Sensitization of hKn Cells to Cisplatinum-induced Cell Death

When hKn cells transfected with no oligonucleotide or the control oligonucleotide ISIS 26080 were treated with 0.5 μg/ml cisplatinum, less than 10% of the cells became apoptotic. Treatment of hKn cells with the combination of the bcl-xl inhibitor ISIS 16009 and the same dose of cisplatinum caused over 25% of the cells to die.

Example 38

Antisense Sensitization of A549 Cells to Taxol-induced Cell Death

A549 cells were treated with 100 nM ISIS 22783 or the 5-mismatch ISIS26080 and taxol at various doses. The percent apoptotic cells was quantitated by propidium iodide staining according to standard methods. Results are shown in Table 13.

TABLE 13

Combination of ISIS 22783 and Taxol

| Compound | Taxol dose (μg/ml) | % Apoptotic cells (approx) | SEQ ID NO: |
|---|---|---|---|
| No oligo | 0 | 2 | |
| | 5 | 3 | |
| | 10 | 7 | |
| | 30 | 16 | |
| ISIS 22783 | 0 | 8 | 33 |
| | 5 | 8 | 33 |
| | 10 | 15 | 33 |
| | 30 | 26 | 33 |
| ISIS 26080 | 0 | 2 | 52 |
| | 5 | 3 | 52 |
| | 10 | 10 | 52 |
| | 30 | 15 | 52 |

Thus th response to the apoptotic stimulus (here a cytotoxic chemotherapeutic drug) has been changed after antisense treatment resulting in increased apoptosis.

Example 39

Treatment of Human Umbilical Vein Endothelial Cells (HUVEC) with Antisense Oligonucleotide to bcl-x and/or Apoptotic Stimuli Human umbilical vein endothelial cells (HUVEC) were obtained from Clonetics (San Diego, Calif.) and cultivated in endothelial growth medium (EGM) supplemented with 10% fetal bovine serum. Cells were used between passages 2 and 5 and were used at approximately 80% confluency. Cells were washed three times with pre-warmed (37° C.) Opti-MEM™. Oligonucleotides were premixed with 10 ug/ml Lipofectin™ in Opti-MEM™ at an oligonucleotide concentration of 50 nM ISIS 16009. Cells were incubated with oligonucleotide for 4 hours at 37° C. after which the medium was removed and replaced with standard growth medium. Treatment with C6-ceramide (Calbiochem, San Diego, Calif.), staurosporine (Calbiochem), or z-VAD.fmk (Calbiochem), if any, was done 24 hours after oligonucleotide treatment. Bcl-xl mRNA levels were measured by Northern blot analysis and found to be decreased to approximately 5% of control, with an apparent $IC_{50}$ of less than 20 nM. Bcl-xl protein levels were measured by Western analysis and found be approximately 5% of control. Apoptotic cells with fragmented DNA were identified by flow cytometry analysis of hypodiploid cells. Inhibition of bcl-x protein (which is virtually all bcl-xl in these cells) caused 10–25% of the cell population to undergo apoptosis.

Example 40

Sensitization of HUVEC Endothelial Cells to Apoptotic Stimuli by the bcl-xl Inhibitor ISIS 16009

Staurosporine (a protein kinase inhibitor) and C6-ceramide (a lipid second messenger) have been shown to induce apoptosis in many cell types. Treatment of HUVEC with low doses of staurosporine (2 nM) or C6-ceramide (5 uM) alone did not cause a significant increase in cellular DNA fragmentation (a measure of apoptosis) over the background of 10–25% apoptotic cells. However, cells treated with ISIS 16009 to reduce levels of bcl-x were more sensitive to these doses of apoptotic stimuli, with over 50% apoptotic cells in samples treated with ISIS 16009 and staurosporine, and over 40% apoptosis in cells treated with ISIS 16009 and ceramide. Thus inhibition of bcl-x sensitizes cells to these apoptotic stimuli. The apoptosis caused by bcl-x inhibition, or bcl-x plus staurosporine or ceramide, was prevented by treatment of cells with the caspase inhibitors z-VAD.fmk or z-DEVD.fmk (Calbiochem, San Diego, Calif.).

Example 41

Measurement of Mitochondrial Dysfunction

To evaluate the mitochondrial transmembrane potential (usually abbreviated as Δψm, cells were incubated with the cationic lipophilic dye MitoTracker Orange CMTMRos (Molecular Probes, Eugene, Oreg.) at a concentration of 150 nM for 15 minutes at 37° C. in the dark. Control cells were simultaneously treated with 50 μM of the protonophores, carbonyl cyanide m-chlorophenylhydrazone (CCCP) (Calbiochem, San Diego, Calif.) which disrupts mitochondrial transmembrane potential. Both adherent and floating cells were collected, washed once with 1x PBS/2% BSA, and fixed in 1 ml PBS containing 4% paraformaldehyde for 15 minutes at room temperature while shaking. Fixed cells were stored in the dark at 4° C. for 1 day prior to analysis by flow cytometry.

Example 42

Effect of bcl-x Inhibition on Mitochondrial Integrity

One proposed mechanism by which cells are protected from apoptosis is by protection of mitochondrial function. Treatment of HUVEC with the bcl-x inhibitor ISIS 16009 resulted in a reduction in mitochondrial transmembrane potential, which was potentiated by either staurosporine or ceramide. The loss of mitochondrial integrity caused by either bcl-x antisense inhibitor alone or antisense plus staurosporine (but not antisense plus ceramide) was prevented by treatment of HUVEC with the caspase inhibitor z-VAD.fmk (Calbiochem, San Diego, Calif.).

Example 43

Additional 2'-MOE Oligonucleotides Designed to Alter Splicing of Human Bcl-xl

An additional series of uniform 2'-MOE oligonucleotides were designed to target the region upstream from or overlapping the 5' splice site at nucleotide 699 of human bcl-xl. The purpose of this was to optimize the effect on splice products, increasing the ratio of bcl-xs/bcl-xl transcripts produced. The oligonucleotides are shown in Table 14. Backbones are phosphorothioate throughout. All nucleotide numbers correspond to those on Genbank accession no. Z23115 except for ISIS 105751 which bridges the splice site, and hybridizes to nucleotides 555–574 of Genbank accession no. U72398, which encodes the unspliced human bcl-x (bcl-x-beta). This target sequence corresponds to ten nucleotides upstream of the 5' splice site (positions 689–698 of Genbank accession no. Z23115) and ten nucleotides of intron 1.

TABLE 14

Additional 2'-MOE oligonucleotides designed to alter splicing of human bcl-xl

| ISIS # | Sequence | Target Region | Target site | Target Genbank acc. no | SEQ ID NO: |
|---|---|---|---|---|---|
| 106260 | GTGGCCATCCAAGCTGCGAT | coding/exon 1L | 630–649 | Z23115 | 53 |
| 106259 | AAGTGGCCATCCAAGCTGCG | coding/exon 1L | 632–651 | Z23115 | 54 |
| 106258 | GTAAGTGGCCATCCAAGCTG | coding/exon 1L | 634–653 | Z23115 | 55 |
| 106257 | AGGTAAGTGGCCATCCAAGC | coding/exon 1L | 636–655 | Z23115 | 56 |
| 106256 | TCAGGTAAGTGGCCATCCAA | coding/exon 1L | 638–657 | Z23115 | 57 |
| 106255 | ATTCAGGTAAGTGGCCATCC | coding/exon 1L | 640–659 | Z23115 | 58 |
| 106254 | TCATTCAGGTAAGTGGCCAT | coding/exon 1L | 642–661 | Z23115 | 59 |
| 106253 | GGTCATTCAGGTAAGTGGCC | coding/exon 1L | 644–663 | Z23115 | 60 |
| 106252 | GTGGTCATTCAGGTAAGTGG | coding/exon 1L | 646–665 | Z23115 | 61 |
| 106251 | AGGTGGTCATTCAGGTAAGT | coding/exon 1L | 648–667 | Z23115 | 62 |
| 106250 | CTAGGTGGTCATTCAGGTAA | coding/exon 1L | 650–669 | Z23115 | 63 |
| 106249 | CTCTAGGTGGTCATTCAGGT | coding/exon 1L | 652–671 | Z23115 | 64 |
| 26066 | ATCCAAGGCTCTAGGTGGTC | coding/exon 1L | 660–679 | Z23115 | 65 |
| 22783 | CTGGATCCAAGGCTCTAGGT | coding/exon 1L | 664–683 | Z23115 | 33 |
| 105751 | TGGTTCTTACCCAGCCGCCG | exon 1L/intron 1 | 555–574 | U72398 | 66 |

TABLE 14-continued

Additional 2'-MOE oligonucleotides
designed to alter splicing of human bcl-xl

| ISIS # | Sequence | Target Region | Target site | Target Genbank acc. no | SEQ ID NO: |
|---|---|---|---|---|---|
| | | | 689–698 | Z23115 | |
| 26080 | CTGGTTACACGACTCCAGGT | | 22783 mismatch | | 52 |

TABLE 15

Effect of antisense oligonucleotides on bcl-xs and bcl-xl

| ISIS # | SEQ ID NO | % CONTROL bcl-xl | bcl-xs/ bcl-xl Fold difference | Target site distance (from 5' end of target site) upstream of bcl-xl 5' splice site |
|---|---|---|---|---|
| no oligo | — | 100 | 1 | — |
| 106260 | 53 | 66 | 12 | 68 |
| 106259 | 54 | 96 | 15 | 66 |
| 106258 | 55 | 66 | 21 | 64 |
| 106257 | 56 | 78 | 13 | 62 |
| 106256 | 57 | 82 | 15 | 60 |
| 106255 | 58 | 64 | 17 | 58 |
| 106254 | 59 | 80 | 13 | 56 |
| 106253 | 60 | 48 | 19 | 54 |
| 106252 | 61 | 72 | 23 | 52 |
| 106251 | 62 | 57 | 25 | 50 |
| 106250 | 63 | 40 | 21 | 48 |
| 106249 | 64 | 47 | 23 | 46 |
| 26066 | 65 | 24 | 37 | 38 |
| 22783 | 33 | 39 | 18 | 34 |
| 105751 | 66 | 34 | 45 | Straddles splice site |
| 26080 | 52 | 77 | 2 | mismatch control |

All of the oligonucleotides shown in the above table were able to increase the bcl-xs/bcl-xl ratio by at least 12 fold and several (106249–106253, 26066, 22783 and 105751) increased the ratio over the previous maximum of approximately 17-fold shown in Table 8. ISIS 105751 and 26066 are highly preferred for increasing the bcl-xs/bcl-xl ratio to 45-fold and 37-fold, respectively. This effect was dose-dependent, as measured for ISIS 26066 at doses from 50 to 400 nM. ISIS 26066 was tested and had no effect on bcl-x-beta (unspliced) levels.

Interestingly, all of the oligonucleotides that targeted a region approximately 15–54 nucleotides upstream of the 5' splice site for bcl-xl are extremely potent redirectors of splicing, indicating that this region may be important for splice site selection. This is supported by the fact that mouse, rat and pig bcl-x sequences are identical to the human sequence from nucleotide 654 (using the numbering of the human sequence in Genbank accession no. Z23115) through the 5' splice site at nucleotide 698. Accordingly, oligonucleotides targeting the region extending approximately 60 nucleotides upstream (5' direction) from the splice site at nucleotide 698 are preferred. Oligonucleotides straddling the splice site are also preferred.

What is claimed is:

1. An antisense compound 8 to 30 nucleotides in length targeted to a nucleic acid molecule encoding a human bcl-x, wherein said antisense compound modulates the expression of human bcl-x, and wherein said antisense compound is an antisense oligonucleotide which comprises at least an 8 nucleobase portion of SEQ ID NO: 43, 44, 46, 53, 54, 55, 56, 57, 58, 59, 60, 61, 62, 63, 64, 65, or 66.

2. The antisense compound of claim 1 wherein the antisense oligonucleotide comprises at least one modified internucleoside linkage.

3. The antisense compound of claim 2 wherein the modified internucleoside linkage of the antisense oligonucleotide is a phosphorothioate linkage, a morpholino linkage or a peptide-nucleic acid linkage.

4. The antisense compound of claim 1 wherein the antisense oligonucleotide comprises at least one modified sugar moiety.

5. The antisense compound of claim 4 wherein the modified sugar moiety of the antisense oligonucleotide is a 2'-O-methoxyethyl sugar moiety or a 2'-dimethylaminooxyethoxy sugar moiety.

6. The antisense compound of claim 4 wherein substantially all sugar moieties of the antisense oligonucleotide are modified sugar moieties.

7. The antisense compound of claim 1 wherein the antisense oligonucleotide comprises at least one modified nucleobase.

8. The antisense compound of claim 7 wherein the modified nucleobase of the antisense oligonucleotide is a 5-methylcytosine.

9. The antisense compound of claim 5 wherein each 2'-O-methoxyethyl modified cytosine nucleobase of the antisense oligonucleotide is a 5-methylcytosine.

10. The antisense compound of claim 1 which is a chimeric oligonucleotide.

11. A composition comprising the antisense compound of claim 1 and a pharmaceutically acceptable carrier or diluent.

12. The composition of claim 11 further comprising a colloidal dispersion system.

13. The antisense compound of claim 1 which is targeted to bcl-xl.

14. The antisense compound of claim 1 which is targeted to a nucleic acid molecule encoding bcl-xl and which preferentially inhibits the expression of bcl-xl.

15. The antisense compound of claim 14 which is targeted to a region of a nucleic acid molecule encoding bcl-xl which is not found in a nucleic acid molecule encoding bcl-xs.

16. The antisense compound of claim 14 which promotes apoptosis.

17. The antisense compound of claim 1 which is targeted to a region of a nucleic acid molecule encoding bcl-xs and which reduces the expression of bcl-xs.

18. The antisense compound of claim 17 which inhibits apoptosis.

19. The antisense compound of claim 1 which alters the ratio of bcl-x isoforms expressed by a cell or tissue.

20. The antisense compound of claim 19 which increases the ratio of bcl-xl to bcl-xs expressed.

21. The antisense compound of claim 19 which decreases the ratio of bcl-xl to bcl-xs expressed.

22. An antisense compound which alters splicing of an RNA encoding human bcl-x, such that the ratio of bcl-xs to bcl-xl is altered, and which is targeted to at least a portion of the region from nucleotides 638 to 698 of SEQ ID NO 1, a nucleic acid encoding human bcl-x.

23. The antisense compound of claim 22 which is an antisense oligonucleotide.

24. The antisense compound of claim 23 wherein the antisense oligonucleotide comprises at least one 2'-O-methoxyethyl sugar moiety or 2'-dimethylaminooxyethoxy sugar moiety.

25. The antisense compound of claim 23 wherein substantially all sugar moieties of the antisense oligonucleotide are modified sugar moieties.

26. An antisense compound which comprises SEQ ID NO: 33, 34, 46, 53, 54, 55, 56, 57, 58, 59, 60, 61, 62, 63, 64, 65 or 66.

27. The antisense compound of claim 26, wherein said antisense compound is an antisense oligonucleotide 8 to 30 nucleotides in length which alters splicing of an RNA encoding a bcl-x gene product, wherein said oligonucleotide is targeted to said bcl-x gene product and comprises at least one 2'-O-methoxyethyl or 2'-dimethylaminooxyethoxy sugar moiety.

28. The antisense oligonucleotide of claim 27 wherein substantially all sugar moieties are 2'-O-methoxyethyl or 2'-dimethylaminooxyethoxy sugar moieties.

29. A method of inhibiting the expression of bcl-x in human cells or tissues in vitro comprising contacting said cells or tissues with the antisense compound of claim 1 so that expression of bcl-x is inhibited.

30. A method of altering the ratio of the isoforms of bcl-x in human cells or tissues in vitro comprising contacting said cells or tissues with the antisense compo claim 1 so that the ratio of the bcl-x isoforms is altered.

31. A method of sensitizing a cell in vitro to an apoptotic stimulus comprising treating the cell with an inhibitor of bcl-x, wherein said inhibitor is the antisense compound of claim 1.

32. The method of claim 31 wherein the apoptotic stimulus is radiation.

33. The method of claim 32 wherein the radiation is ultraviolet radiation.

34. The method of claim 31 wherein the apoptotic stimulus is a cancer chemotherapeutic drug.

35. The method of claim 34 wherein the cancer chemotherapeutic drug is VP-16, cisplatinum or taxol.

36. The method of claim 31 wherein the apoptotic stimulus is a cellular signaling molecule.

37. The method of claim 36 wherein the apoptotic stimulus is ceramide or a cytokine.

38. A method of sensitizing a cell in vitro to an apoptotic stimulus comprising treating the cell with an antisense inhibitor of bcl-xl wherein the antisense inhibitor of bcl-xl has a sequence comprising at least an 8-nucleobase portion of SEQ ID NO: 31 or 33.

39. The method of claim 38 wherein the apoptotic stimulus is ceramide is staurosporine.

40. The method of claim 31 wherein said apoptotic stimulus causes mitochondrial dysfunction.

41. The method of claim 40 wherein said mitochondrial dysfunction is loss of mitochondrial membrane potential.

42. A method of inducing mitochondrial dysfunction in a cell comprising treating the cell with an inhibitor of bcl-xl, wherein said inhibitor is the antisense compound of claim 1.

43. The method of claim 42 further comprising exposing the cell to an apoptotic stimulus.

44. The method of claim 43 wherein the apoptotic stimulus is radiation.

45. The method of claim 44 wherein the radiation is ultraviolet radiation.

46. The method of claim 43 wherein the apoptotic stimulus is a cancer chemotherapeutic drug.

47. The method of claim 46 wherein the cancer chemotherapeutic drug is VP-16, cisplatinum or taxol.

48. The method of claim 43 wherein the apoptotic stimulus is ceramide or staurosporine.

49. A method of inducing mitochondrial dysfunction in a cell comprising treating the cell in vitro with an antisense inhibitor of bcl-xl wherein the antisense inhibitor of bcl-xl has a sequence comprising at least an 8-nucleobase portion of SEQ ID NO: 31 or 33.

50. The method of claim 42 wherein the mitochondrial dysfunction is loss of mitochondrial membrane potential.

\* \* \* \* \*

SEQUENCE LISTING

```
<160> NUMBER OF SEQ ID NOS: 66

<210> SEQ ID NO 1
<211> LENGTH: 926
<212> TYPE: DNA
<213> ORGANISM: Homo sapiens
<220> FEATURE:
<221> NAME/KEY: CDS
<222> LOCATION: (135)..(836)
<300> PUBLICATION INFORMATION:
<308> DATABASE ACCESSION NUMBER: L20121 Genbank
<309> DATABASE ENTRY DATE: 1994-07-26

<400> SEQUENCE: 1
gaatctcttt ctctcccttc agaatcttat cttggctttg gatcttagaa gagaatcact     60
aaccagagac gagactcagt gagtgagcag gtgttttgga caatggactg gttgagccca    120
tccctattat aaaa atg tct cag agc aac cgg gag ctg gtg gtt gac ttt     170
              Met Ser Gln Ser Asn Arg Glu Leu Val Val Asp Phe
                1               5                  10 ctc tcc tac aag ctt tcc cag aaa gga tac agc tgg agt cag ttt agt    218
Leu Ser Tyr Lys Leu Ser Gln Lys Gly Tyr Ser Trp Ser Gln Phe Ser
             15                  20                  25
```

```
gat gtg gaa gag aac agg act gag gcc cca gaa ggg act gaa tcg gag    266
Asp Val Glu Glu Asn Arg Thr Glu Ala Pro Glu Gly Thr Glu Ser Glu
         30                  35                  40 atg gag acc ccc agt gcc atc aat ggc aac cca tcc tgg cac ctg gca    314
Met Glu Thr Pro Ser Ala Ile Asn Gly Asn Pro Ser Trp His Leu Ala
 45                  50                  55                  60 gac agc ccc gcg gtg aat gga gcc act gcg cac agc agc agt ttg gat    362
Asp Ser Pro Ala Val Asn Gly Ala Thr Ala His Ser Ser Ser Leu Asp
                     65                  70                  75 gcc cgg gag gtg atc ccc atg gca gca gta aag caa gcg ctg agg gag    410
Ala Arg Glu Val Ile Pro Met Ala Ala Val Lys Gln Ala Leu Arg Glu
                         80                  85                  90 gca ggc gac gag ttt gaa ctg cgg tac cgg cgg gca ttc agt gac ctg    458
Ala Gly Asp Glu Phe Glu Leu Arg Tyr Arg Arg Ala Phe Ser Asp Leu
             95                 100                 105 aca tcc cag ctc cac atc acc cca ggg aca gca tat cag agc ttt gaa    506
Thr Ser Gln Leu His Ile Thr Pro Gly Thr Ala Tyr Gln Ser Phe Glu
    110                 115                 120 cag gta gtg aat gaa ctc ttc cgg gat ggg gta aac tgg ggt cgc att    554
Gln Val Val Asn Glu Leu Phe Arg Asp Gly Val Asn Trp Gly Arg Ile
125                 130                 135                 140 gtg gcc ttt ttc tcc ttc ggc ggg gca ctg tgc gtg gaa agc gta gac    602
Val Ala Phe Phe Ser Phe Gly Gly Ala Leu Cys Val Glu Ser Val Asp
                145                 150                 155 aag gag atg cag gta ttg gtg agt cgg atc gca gct tgg atg gcc act    650
Lys Glu Met Gln Val Leu Val Ser Arg Ile Ala Ala Trp Met Ala Thr
            160                 165                 170 tac ctg aat gac cac cta gag cct tgg atc cag gag aac ggc ggc tgg    698
Tyr Leu Asn Asp His Leu Glu Pro Trp Ile Gln Glu Asn Gly Gly Trp
        175                 180                 185 gat act ttt gtg gaa ctc tat ggg aac aat gca gca gcc gag agc cga    746
Asp Thr Phe Val Glu Leu Tyr Gly Asn Asn Ala Ala Ala Glu Ser Arg
    190                 195                 200 aag ggc cag gaa cgc ttc aac cgc tgg ttc ctg acg ggc atg act gtg    794
Lys Gly Gln Glu Arg Phe Asn Arg Trp Phe Leu Thr Gly Met Thr Val
205                 210                 215                 220 gcc ggc gtg gtt ctg ctg ggc tca ctc ttc agt cgg aaa tga            836
Ala Gly Val Val Leu Leu Gly Ser Leu Phe Ser Arg Lys
                225                 230 ccagacactg accatccact ctaccctccc accccttct ctgctccacc acatcctccg    896
tccagccgcc attgccacca ggagaacccg                                    926

<210> SEQ ID NO 2
<211> LENGTH: 233
<212> TYPE: PRT
<213> ORGANISM: Homo sapiens

<400> SEQUENCE: 2

Met Ser Gln Ser Asn Arg Glu Leu Val Val Asp Phe Leu Ser Tyr Lys
 1               5                  10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Ala His Ser Ser Ser Leu Asp Ala Arg Glu Val
 65                  70                  75                  80
```

```
Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cgggttctcc tggtggcaat                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cagtgtctgg tcatttccga                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agcccagcag aaccacgccg                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gttgaagcgt tcctggccct                                            20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cagtgccccg ccgaaggaga                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tcgcctgcct ccctcagcgc                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cagtggctcc attcaccgcg                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
attcagtccc ttctggggcc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
aaagtcaacc accagctccc                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ccggttgctc tgagacattt                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
accagtccat tgtccaaaac                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gaagggagag aaagagattc                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tcattcacta cctgttcaaa                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
agcccaccag aaggaccccg                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cagtggctct caccgcatcg                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
cagcccgcct gcgaaggaga                                            20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
agcgcagaac caccacgccg                                            20

<210> SEQ ID NO 20

-continued

<211> LENGTH: 20
<212> TYPE: DNA
<213> ORGANISM: Artificial Sequence
<220> FEATURE:
<223> OTHER INFORMATION: Synthetic

<400> SEQUENCE: 20
taatagggat gggctcaacc                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
tcccggttgc tctgagacat                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gggcctcagt cctgttctct                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tccatctccg attcagtccc                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
aggtgccagg atgggttgcc                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
agtggctcca ttcaccgcgg                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
cttgctttac tgctgccatg                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gccggtaccg cagttcaaac                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
ctgttcaaag ctctgatatg                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
taccccatcc cggaagagtt                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
aaaggccaca atgcgacccc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ctacgctttc cacgcacagt                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tccaagctgc gatccgactc                                              20

<210> SEQ ID NO 33
<211> LENGTH: 20
<212> TYPE: DNA

```
<213> ORGANISM: Artificial Sequence
<220> FEATURE:
<223> OTHER INFORMATION: Synthetic

<400> SEQUENCE: 33
ctggatccaa ggctctaggt                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ccagccgccg ttctcctgga                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tagagttcca caaaagtatc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
agcgttcctg gccctttcgg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gtcatgcccg tcaggaacca                                              20

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
tgagcccagc agaccacgc                                               19

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gagggtagag tggatggtca                                              20
```

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ggaggatgtg gtggagcaga                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41 gacatcccttt tccccctcgg                                              20

<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Asp Glu Val Asp
 1

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
ctccgatgtc ccctcaaagt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
tcacgttggc gcttagccat                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
caaaagtatc ccagccgccg                                               20

<210> SEQ ID NO 46
<211> LENGTH: 20
<212> TYPE: DNA
<213> ORGANISM: Artificial Sequence

```
<220> FEATURE:
<223> OTHER INFORMATION: Synthetic

<400> SEQUENCE: 46
gccgccgttc tcctggatcc                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gttcctggcc ctttcggctc                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
caggaaccag cggttgaagc                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
ccggccacag tcatgcccgt                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tgtagcccag cagaaccacg                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
cgacacgtac ctctcgcatt                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ctggttacac gactccaggt                                               20
```

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gtggccatcc aagctgcgat                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
aagtggccat ccaagctgcg                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gtaagtggcc atccaagctg                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
aggtaagtgg ccatccaagc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tcaggtaagt ggccatccaa                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
attcaggtaa gtggccatcc                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic

```
<400> SEQUENCE: 59
tcattcaggt aagtggccat                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ggtcattcag gtaagtggcc                                                    20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gtggtcattc aggtaagtgg                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
aggtggtcat tcaggtaagt                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
ctaggtggtc attcaggtaa                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ctctaggtgg tcattcaggt                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
atccaaggct ctaggtggtc                                                    20

<210> SEQ ID NO 66
```

-continued

```
<211> LENGTH: 20
<212> TYPE: DNA
<213> ORGANISM: Artificial Sequence
<220> FEATURE:
<223> OTHER INFORMATION: Synthetic

<400> SEQUENCE: 66
tggttcttac ccagccgccg                                              20
```